United States Patent
Banister et al.

(10) Patent No.: US 9,995,295 B2
(45) Date of Patent: Jun. 12, 2018

(54) FLUID METERING DEVICE (75) Inventors: Mark Banister, Tucson, AZ (US); Dale L. Fanter, Sahuarita, AZ (US)

(73) Assignee: MEDIPACS, INC., Tucson, AZ (US)

(*) Notice: Subject to any disclaimer, the term of this patent is extended or adjusted under 35 U.S.C. 154(b) by 443 days.

(21) Appl. No.: 12/745,880

(22) PCT Filed: Dec. 3, 2008

(86) PCT No.: PCT/US2008/085421
§ 371 (c)(1),
(2), (4) Date: Jun. 2, 2010

(87) PCT Pub. No.: WO2009/073734
PCT Pub. Date: Jun. 11, 2009

(65) Prior Publication Data
US 2010/0268200 A1 Oct. 21, 2010

Related U.S. Application Data (60) Provisional application No. 60/992,003, filed on Dec. 3, 2007.

(51) Int. Cl.
*A61M 31/00* (2006.01)
*F04B 43/02* (2006.01)
(Continued)

(52) U.S. Cl.
CPC .......... *F04B 43/02* (2013.01); *A61M 5/14276* (2013.01); *A61M 5/14593* (2013.01);
(Continued)

(58) Field of Classification Search
CPC .......... A61M 2005/14513; A61M 2205/0272; A61M 2205/0277; A61M 2230/201;
(Continued)

(56) References Cited

U.S. PATENT DOCUMENTS 3,029,743 A 4/1962 Johns .......................... 103/150
3,922,328 A 11/1975 Johnson
(Continued)

FOREIGN PATENT DOCUMENTS

CA 2 477 181 4/2004
CN 1080829 3/2002 .............. F04B 35/00
(Continued)

OTHER PUBLICATIONS

PCT International Search Report and International Preliminary Report on Patentability, dated Oct. 22, 2004, PCT/US04/005922.
(Continued)

*Primary Examiner* — Quynh-Nhu H Vu
(74) *Attorney, Agent, or Firm* — Hayes Soloway P.C.

(57) ABSTRACT

A device for metering fluids comprising a fluid chamber with one inlet or outlet port, at least one sidewall and a movable separator that is in contact with and separates the fluid in the chamber from the other components of the device, a porous actuator housing and wicking material, a flexible polymer actuator material in contact with the porous actuator housing and the moveable separator, an actuator hydrating solution reservoir with at least one sidewall, an inlet port, and in fluid contact with porous actuator housing, a fluid gate located at some point between actuator hydrating solution reservoir and the polymer actuator, effectively keeping actuator dry, and an external shell to hold all components so that the polymer actuator can only move in a direction and apply pressure to the separator in contact with the fluid in the fluid chamber, thereby dispensing fluid from fluid chamber.

59 Claims, 3 Drawing Sheets

(51) Int. Cl.
*A61M 5/142* (2006.01)
*A61M 5/145* (2006.01)

(52) U.S. Cl.
CPC .............. *A61M 2005/14513* (2013.01); *F05C 2231/00* (2013.01); *F05C 2251/08* (2013.01)

(58) Field of Classification Search
CPC .......... A61M 5/14244; A61M 5/14276; A61M 5/14593; A61M 5/148; F04B 43/02; F04B 43/043; F04B 43/082; Y10T 137/6137
USPC ................................................ 604/891.1, 246
See application file for complete search history.

(56) References Cited

U.S. PATENT DOCUMENTS

| | | | |
|---|---|---|---|
| 4,034,380 A | 7/1977 | Isayama | 347/19 |
| 4,111,202 A | 9/1978 | Theeuwes | |
| 4,190,411 A | 2/1980 | Fujimoto | |
| 4,203,440 A | 5/1980 | Theeuwes | |
| 4,299,220 A * | 11/1981 | Dorman | 604/118 |
| 4,327,725 A * | 5/1982 | Cortese et al. | 424/427 |
| 4,395,719 A | 7/1983 | Majewski et al. | 347/68 |
| 4,423,166 A | 12/1983 | Moriarty et al. | 523/414 |
| 4,432,699 A | 2/1984 | Beckman et al. | 417/63 |
| 4,449,893 A | 5/1984 | Beckman | 417/322 |
| 4,449,983 A | 5/1984 | Cortese et al. | 604/892 |
| 4,507,363 A | 3/1985 | Chow et al. | 428/418 |
| 4,538,607 A | 9/1985 | Saul | 128/207.16 |
| 4,551,139 A | 11/1985 | Plaas et al. | |
| 4,559,038 A | 12/1985 | Berg et al. | |
| 4,595,583 A | 6/1986 | Eckenhoff et al. | |
| 4,624,847 A | 11/1986 | Ayer et al. | |
| 4,624,848 A | 11/1986 | Lee | |
| 4,650,469 A | 3/1987 | Berg et al. | |
| 4,655,767 A | 4/1987 | Woodard et al. | |
| 4,663,149 A | 5/1987 | Eckenhoff et al. | |
| 4,675,174 A | 6/1987 | Eckenhoff | |
| 4,723,958 A | 2/1988 | Pope et al. | |
| 4,772,474 A | 9/1988 | Eckenhoff et al. | |
| 4,781,714 A | 11/1988 | Eckenhoff et al. | |
| 4,808,084 A | 2/1989 | Tsubouchi et al. | 417/322 |
| 4,810,535 A | 3/1989 | McCollum et al. | 427/410 |
| 4,842,493 A | 6/1989 | Nilsson | 417/322 |
| 4,863,456 A | 9/1989 | Stephens et al. | |
| 4,948,592 A | 8/1990 | Ayer et al. | |
| 4,963,141 A | 10/1990 | Eckenhoff | |
| 5,000,957 A | 3/1991 | Eckenhoff et al. | |
| 5,034,229 A | 7/1991 | Magruder et al. | |
| 5,037,420 A | 8/1991 | Magruder et al. | |
| 5,059,423 A | 10/1991 | Magruder et al. | |
| 5,061,242 A | 10/1991 | Sampson | |
| 5,070,560 A | 12/1991 | Wilkinson | 5/455 |
| 5,100,933 A | 3/1992 | Tanaka et al. | 523/300 |
| 5,105,983 A | 4/1992 | Sancoff et al. | 222/103 |
| 5,110,596 A | 5/1992 | Magruder et al. | |
| 5,175,246 A | 12/1992 | Smith | 523/111 |
| 5,192,197 A * | 3/1993 | Culp | 417/322 |
| 5,232,702 A | 8/1993 | Pfister et al. | |
| 5,246,705 A | 9/1993 | Venkatraman et al. | |
| 5,275,853 A | 1/1994 | Silvis | 428/35.4 |
| 5,279,544 A | 1/1994 | Gross et al. | |
| 5,279,565 A | 1/1994 | Klein et al. | |
| 5,284,133 A | 2/1994 | Burns et al. | |
| 5,300,299 A | 4/1994 | Sweet et al. | |
| 5,304,121 A | 4/1994 | Sahatjian | |
| 5,327,041 A | 7/1994 | Culp | 310/328 |
| 5,328,696 A | 7/1994 | Noel | |
| 5,336,057 A | 8/1994 | Fukuda et al. | 417/395 |
| 5,348,746 A | 9/1994 | Dong et al. | |
| 5,354,264 A | 10/1994 | Bae et al. | |
| 5,376,378 A | 12/1994 | Li et al. | |
| 5,380,760 A | 1/1995 | Wendel et al. | |
| 5,412,821 A | 5/1995 | Wilkinson | 5/455 |
| 5,429,585 A | 7/1995 | Liang | 601/15 |
| 5,431,921 A | 7/1995 | Thombre | |
| 5,474,783 A | 12/1995 | Miranda et al. | |
| 5,498,255 A | 3/1996 | Wong | |
| 5,520,643 A | 5/1996 | Ensminger et al. | 604/93 |
| 5,546,932 A | 8/1996 | Galli | |
| 5,573,668 A | 11/1996 | Grosh et al. | |
| 5,587,237 A | 12/1996 | Korpman et al. | |
| RE35,474 E | 3/1997 | Woodard et al. | |
| 5,618,899 A | 4/1997 | Appelt et al. | |
| 5,622,482 A | 4/1997 | Lee | 417/321 |
| 5,630,709 A | 5/1997 | Bar-Cohen | 417/322 |
| 5,633,009 A | 5/1997 | Kenealy et al. | |
| 5,645,855 A | 7/1997 | Lorenz | |
| 5,656,286 A | 8/1997 | Miranda et al. | |
| 5,674,192 A | 10/1997 | Sahatjian et al. | |
| 5,687,748 A | 11/1997 | Conrad et al. | |
| 5,692,256 A | 12/1997 | Kramer et al. | 5/624 |
| 5,714,160 A | 2/1998 | Magruder et al. | |
| 5,718,700 A | 2/1998 | Edgren et al. | |
| 5,779,668 A | 7/1998 | Grabenkort | |
| 5,798,600 A | 8/1998 | Sager et al. | 310/330 |
| 5,810,001 A | 9/1998 | Genga et al. | 128/202.27 |
| 5,823,178 A | 10/1998 | Lloyd et al. | |
| 5,891,463 A | 4/1999 | Bello et al. | |
| 5,916,968 A | 6/1999 | Hariharan et al. | |
| 5,939,477 A | 8/1999 | Pretzer et al. | |
| 5,951,999 A | 9/1999 | Therriault et al. | |
| 5,954,706 A | 9/1999 | Sahatjian | |
| 5,955,549 A | 9/1999 | Chang | 525/418 |
| 5,961,298 A | 10/1999 | Bar-Cohen et al. | 417/322 |
| 5,979,892 A | 11/1999 | Smith | 271/267 |
| 5,997,501 A | 12/1999 | Gross et al. | |
| 6,004,115 A * | 12/1999 | da Costa | 417/413.2 |
| 6,010,485 A | 1/2000 | Buch-Rasmussen et al. | |
| 6,024,976 A | 2/2000 | Miranda et al. | |
| 6,066,325 A | 5/2000 | Wallace et al. | |
| RE36,754 E | 6/2000 | Noel | |
| 6,074,178 A * | 6/2000 | Bishop et al. | 417/322 |
| 6,074,179 A | 6/2000 | Jokela et al. | 417/322 |
| 6,106,245 A | 8/2000 | Cabuz | 417/322 |
| 6,109,852 A | 8/2000 | Shahinpoor et al. | 414/1 |
| 6,143,138 A | 11/2000 | Becker | 204/157.15 |
| 6,152,898 A | 11/2000 | Olsen | |
| 6,157,113 A | 12/2000 | Hunter et al. | 310/300 |
| 6,165,155 A | 12/2000 | Jacobsen et al. | |
| 6,174,546 B1 | 1/2001 | Therriault et al. | |
| 6,180,133 B1 | 1/2001 | Quan et al. | |
| 6,183,434 B1 | 2/2001 | Eppstein | |
| 6,184,608 B1 | 2/2001 | Cabuz et al. | 310/309 |
| 6,193,996 B1 | 2/2001 | Effing et al. | |
| 6,206,850 B1 | 3/2001 | O'Neil | |
| 6,210,712 B1 | 4/2001 | Edgren et al. | |
| 6,213,739 B1 | 4/2001 | Phallen et al. | 417/478 |
| 6,221,383 B1 | 4/2001 | Miranda et al. | |
| 6,223,369 B1 | 5/2001 | Maier et al. | 5/713 |
| 6,249,076 B1 | 6/2001 | Madden et al. | 310/363 |
| 6,277,401 B1 | 8/2001 | Bello et al. | |
| 6,312,715 B1 | 11/2001 | Cantor et al. | |
| 6,316,022 B1 | 11/2001 | Mantelle et al. | |
| 6,319,245 B1 | 11/2001 | Berrigan | |
| 6,336,907 B1 | 1/2002 | Dono et al. | 601/150 |
| 6,337,086 B1 | 1/2002 | Kanios et al. | |
| 6,352,715 B1 | 3/2002 | Hwang et al. | |
| 6,365,178 B1 | 4/2002 | Venkateshwaran et al. | |
| 6,365,185 B1 | 4/2002 | Ritschel et al. | |
| 6,368,318 B1 | 4/2002 | Visuri et al. | |
| 6,378,292 B1 | 4/2002 | Youngner | 60/224 |
| 6,387,077 B1 | 5/2002 | Klibanov et al. | |
| 6,392,777 B1 | 5/2002 | Elliott et al. | 359/244 |
| 6,409,716 B1 | 6/2002 | Sahatjian et al. | |
| 6,450,773 B1 | 9/2002 | Upton | 417/53 |
| 6,461,644 B1 | 10/2002 | Jackson et al. | |
| 6,464,476 B2 | 10/2002 | Ross et al. | 417/478 |
| 6,471,686 B1 | 10/2002 | Berrigan | |
| 6,475,639 B2 | 11/2002 | Shahinpoor et al. | 428/614 |
| 6,490,483 B2 | 12/2002 | Willis | 604/20 |
| 6,531,152 B1 | 3/2003 | Lerner et al. | |
| 6,537,194 B1 | 3/2003 | Winkler | |
| 6,578,245 B1 | 6/2003 | Chatterjee et al. | 29/25.35 |

(56) References Cited

U.S. PATENT DOCUMENTS

| | | |
|---|---|---|
| 6,586,512 B1 | 7/2003 | Dukes .................. 524/377 |
| 6,632,522 B1 | 10/2003 | Hyde et al. |
| 6,664,718 B2 | 12/2003 | Pelrine et al. |
| 6,682,318 B2 | 1/2004 | Takeuchi et al. ............ 417/322 |
| 6,682,500 B2* | 1/2004 | Soltanpour ........ A61F 9/00781 604/521 |
| 6,685,442 B2* | 2/2004 | Chinn et al. .................. 417/321 |
| 6,726,678 B1 | 4/2004 | Nelson ..................... 604/891.1 |
| 6,766,817 B2 | 7/2004 | da Silva .................. F04F 10/00 |
| 6,791,003 B1 | 9/2004 | Choi et al. |
| 6,796,970 B1 | 9/2004 | Klitmose et al. |
| 6,809,462 B2 | 10/2004 | Pelrine et al. ................ 310/319 |
| 6,864,295 B2 | 3/2005 | Mitarai ..................... 521/50.5 |
| 6,869,275 B2 | 3/2005 | Dante et al. ............... 417/413.2 |
| 6,876,135 B2 | 4/2005 | Pelrine et al. ................ 310/339 |
| 6,902,704 B2 | 6/2005 | Wilson ........................ 422/100 |
| 6,940,211 B2 | 9/2005 | Pelrine et al. ................ 310/330 |
| 6,948,636 B1 | 9/2005 | Fischer et al. ............... 222/103 |
| 6,949,079 B1 | 9/2005 | Westberg et al. ............. 604/6.11 |
| 6,955,923 B2 | 10/2005 | Hartting ..................... 436/180 |
| 6,960,864 B2 | 11/2005 | Urano et al. ................. 310/307 |
| 7,285,255 B2 | 10/2007 | Kadlec et al. ............ A61L 2/16 |
| 7,411,792 B2 | 8/2008 | Richards et al. ............. 361/704 |
| 7,453,187 B2 | 11/2008 | Richards et al. ............. 310/339 |
| 7,458,956 B1 | 12/2008 | Adams ........................ 604/158 |
| 7,544,260 B2 | 6/2009 | Banister et al. .................. 149/2 |
| 7,553,903 B2 | 6/2009 | Riegel et al. ................. 524/599 |
| 7,700,129 B2 | 4/2010 | Ito et al. ...................... 424/486 |
| 7,820,427 B2 | 10/2010 | Unger et al. ............... 435/286.5 |
| 8,190,270 B2 | 5/2012 | Wingeier et al. ............. 607/116 |
| 2001/0053383 A1 | 12/2001 | Miranda et al. |
| 2002/0001571 A1 | 1/2002 | Wu ................................ 424/61 |
| 2002/0004064 A1 | 1/2002 | Quan et al. |
| 2002/0007014 A1 | 1/2002 | Hyde et al. |
| 2002/0010412 A1 | 1/2002 | Eppstein |
| 2002/0015733 A1 | 2/2002 | Flashner-Barak et al. |
| 2002/0043895 A1 | 4/2002 | Richards et al. ............. 310/328 |
| 2002/0106402 A1 | 8/2002 | Hartwig |
| 2002/0115740 A1 | 8/2002 | Beuhler et al. ............... 522/152 |
| 2002/0128572 A1 | 9/2002 | Chang ......................... 601/148 |
| 2002/0128618 A1 | 9/2002 | Frenz et al. .................. 604/368 |
| 2002/0147208 A1 | 10/2002 | Fleshner-Barak et al. |
| 2002/0156463 A1 | 10/2002 | Berrigan |
| 2002/0173745 A1* | 11/2002 | Santini et al. .................. 604/67 |
| 2002/0183738 A1 | 12/2002 | Chee et al. |
| 2002/0193754 A1 | 12/2002 | Cho |
| 2003/0014036 A1 | 1/2003 | Varner et al. |
| 2003/0051292 A1 | 3/2003 | Ferrand et al. .................... 5/600 |
| 2003/0054025 A1 | 3/2003 | Cantor et al. |
| 2003/0065303 A1 | 4/2003 | Wellman et al. |
| 2003/0069359 A1 | 4/2003 | Torii et al. .................... 525/178 |
| 2003/0072792 A1 | 4/2003 | Flanigan et al. |
| 2003/0108590 A1 | 6/2003 | Peery et al. |
| 2003/0124189 A1 | 7/2003 | Zentner et al. |
| 2003/0135158 A1 | 7/2003 | Gonnelli |
| 2003/0139495 A1 | 7/2003 | Zentner et al. |
| 2003/0143257 A1 | 7/2003 | Fleshner-Barak et al. |
| 2003/0152616 A1 | 8/2003 | Hartwig |
| 2003/0153900 A1 | 8/2003 | Aceti et al. |
| 2003/0156953 A1 | 8/2003 | Chinn et al. .................. 417/332 |
| 2003/0163099 A1 | 8/2003 | Wermeling et al. |
| 2003/0216683 A1 | 11/2003 | Shekalim |
| 2003/0232198 A1 | 12/2003 | Lamberti et al. |
| 2004/0030262 A1 | 2/2004 | Fisher et al. |
| 2004/0068224 A1 | 4/2004 | Couvillon et al. .............. 604/67 |
| 2004/0092865 A1 | 5/2004 | Flaherty et al. |
| 2004/0102762 A1 | 5/2004 | Gilbert |
| 2004/0106893 A1 | 6/2004 | Hunter |
| 2004/0106894 A1 | 6/2004 | Hunter |
| 2004/0112442 A1 | 6/2004 | Maerkl et al. ................. 137/597 |
| 2004/0133159 A1 | 7/2004 | Haider et al. |
| 2004/0138603 A1 | 7/2004 | Cleary et al. |
| 2004/0142023 A1 | 7/2004 | Hartwig |
| 2004/0149288 A1 | 8/2004 | Koch |
| 2004/0176502 A1 | 9/2004 | Raymond et al. ............. 523/416 |
| 2004/0176748 A1 | 9/2004 | Abramson et al. |
| 2004/0186419 A1 | 9/2004 | Cho |
| 2004/0202708 A1 | 10/2004 | Roehrig et al. |
| 2004/0204677 A1 | 10/2004 | Wellman et al. |
| 2004/0219194 A1 | 11/2004 | Finckh et al. |
| 2004/0220548 A1 | 11/2004 | Heruth et al. |
| 2004/0234401 A1* | 11/2004 | Banister ................ F04B 43/043 417/474 |
| 2004/0242709 A1 | 12/2004 | Oguro et al. .................... 521/27 |
| 2004/0265545 A1 | 12/2004 | McKean et al. ............... 428/189 |
| 2005/0033230 A1 | 2/2005 | Alchas et al. |
| 2005/0043657 A1 | 2/2005 | Couvillon .................... 601/134 |
| 2005/0058695 A1 | 3/2005 | Anigbogu et al. |
| 2005/0137577 A1 | 6/2005 | Heruth et al. |
| 2005/0137578 A1 | 6/2005 | Heruth et al. |
| 2005/0137579 A1 | 6/2005 | Heruth et al. |
| 2005/0261631 A1 | 11/2005 | Clarke et al. |
| 2005/0273081 A1 | 12/2005 | Olsen |
| 2005/0273082 A1 | 12/2005 | Olsen |
| 2005/0287214 A1 | 12/2005 | Ayer et al. |
| 2006/0021614 A1 | 2/2006 | Wermeling et al. |
| 2006/0076540 A1 | 4/2006 | Zama et al. .................. 252/500 |
| 2006/0078603 A1 | 4/2006 | Nguyen |
| 2006/0078604 A1 | 4/2006 | Kanios et al. |
| 2006/0084942 A1 | 4/2006 | Kim et al. |
| 2006/0089619 A1 | 4/2006 | Ginggen .................... 604/891.1 |
| 2006/0094985 A1 | 5/2006 | Aceti et al. |
| 2006/0094989 A1 | 5/2006 | Scott et al. ....................... 601/5 |
| 2006/0110596 A1 | 5/2006 | Palasz et al. |
| 2006/0135911 A1 | 6/2006 | Mittur |
| 2006/0142478 A1 | 6/2006 | Luo ............................ 525/54.1 |
| 2006/0142875 A1 | 6/2006 | Keyes et al. ..................... 700/1 |
| 2006/0146475 A1 | 7/2006 | Zhong et al. ............... 361/301.1 |
| 2006/0183216 A1 | 8/2006 | Handique et al. ......... 435/287.1 |
| 2006/0188558 A1 | 8/2006 | Jackson et al. |
| 2006/0195057 A1 | 8/2006 | Kriesel et al. .................. 604/19 |
| 2006/0200083 A1 | 9/2006 | Freyman et al. .............. 604/181 |
| 2006/0204532 A1 | 9/2006 | John |
| 2006/0213674 A1 | 9/2006 | Dierker, Jr. et al. |
| 2006/0276744 A1 | 12/2006 | Falk |
| 2007/0021697 A1 | 1/2007 | Ginther et al. |
| 2007/0031495 A1 | 2/2007 | Eppstein et al. |
| 2007/0052139 A1 | 3/2007 | Gilbert |
| 2007/0078376 A1 | 4/2007 | Smith |
| 2007/0082038 A1 | 4/2007 | Gale et al. |
| 2007/0088267 A1 | 4/2007 | Shekalim |
| 2007/0092570 A1 | 4/2007 | Missel et al. |
| 2007/0098771 A1 | 5/2007 | Audett et al. |
| 2007/0098772 A1 | 5/2007 | Westcott et al. |
| 2007/0100355 A1 | 5/2007 | Bonde et al. |
| 2007/0104771 A1 | 5/2007 | Audett et al. |
| 2007/0134310 A1 | 6/2007 | Nedberge et al. |
| 2007/0148218 A1 | 6/2007 | Gordon |
| 2007/0190150 A1 | 8/2007 | Ito et al. ....................... 424/486 |
| 2007/0224253 A1 | 9/2007 | Franklin |
| 2007/0260201 A1 | 11/2007 | Prausnitz et al. |
| 2007/0269522 A1 | 11/2007 | Wold |
| 2007/0293826 A1 | 12/2007 | Wall et al. |
| 2008/0004421 A1 | 1/2008 | Chenault ..................... 528/310 |
| 2008/0009800 A1 | 1/2008 | Nickel |
| 2008/0015494 A1 | 1/2008 | Santini, Jr. et al. |
| 2008/0033228 A1 | 2/2008 | Rastegar et al. ................ 600/16 |
| 2008/0039791 A1 | 2/2008 | Abboud et al. ............... 604/113 |
| 2008/0058706 A1 | 3/2008 | Zhang et al. |
| 2008/0063698 A1 | 3/2008 | Hartwig |
| 2008/0091139 A1* | 4/2008 | Srinivasan et al. .............. 604/68 |
| 2008/0110463 A1 | 5/2008 | Hajgato et al. |
| 2008/0125744 A1 | 5/2008 | Treacy |
| 2008/0152592 A1 | 6/2008 | Rebec |
| 2008/0167641 A1 | 7/2008 | Hansen et al. |
| 2008/0183144 A1 | 7/2008 | Trautman et al. |
| 2008/0195018 A1 | 8/2008 | Larson et al. ................... 602/53 |
| 2008/0208107 A1 | 8/2008 | McRae et al. |
| 2008/0214987 A1 | 9/2008 | Xu |
| 2008/0221552 A1 | 9/2008 | Leonard |
| 2008/0234656 A1 | 9/2008 | Pettis et al. |
| 2008/0312610 A1 | 12/2008 | Binks et al. |
| 2008/0317615 A1 | 12/2008 | Banister ..................... 417/413.1 |
| 2009/0007904 A1 | 1/2009 | Schuster et al. |

(56) References Cited

U.S. PATENT DOCUMENTS

| | | |
|---|---|---|
| 2009/0020521 A1 | 1/2009 | Blaszczykiewicz et al. .. 219/529 |
| 2009/0026069 A1 | 1/2009 | Liao et al. ............... 204/274 |
| 2009/0041833 A1 | 2/2009 | Bettinger et al. |
| 2009/0042970 A1 | 2/2009 | Herschkowitz et al. |
| 2009/0048555 A1 | 2/2009 | Stryker et al. |
| 2009/0060986 A1 | 3/2009 | Yum et al. |
| 2009/0085444 A1 | 4/2009 | Alvarez Icaza Rivera et al. ............. 310/365 |
| 2009/0099545 A1 | 4/2009 | Nilsson et al. |
| 2009/0118662 A1 | 5/2009 | Schnall |
| 2009/0221971 A1 | 9/2009 | Mejlhede et al. |
| 2009/0227988 A1 | 9/2009 | Wood, Jr. et al. ....... 604/891.1 |
| 2009/0232685 A1 | 9/2009 | Kamitani et al. ........ 417/413.2 |
| 2009/0317442 A1 | 12/2009 | Banister et al. ............ 424/423 |
| 2010/0004638 A1 | 1/2010 | Gibson ............... 604/891.1 |
| 2010/0074953 A1 | 3/2010 | Chaouk et al. ............ 424/484 |
| 2011/0172645 A1 | 7/2011 | Moga et al. |
| 2013/0172180 A1 | 7/2013 | Naumann ................ 502/402 |
| 2013/0337566 A1 | 12/2013 | Schmidt ............... 435/404 |
| 2014/0048558 A1 | 2/2014 | Lee ..................... 222/95 |

FOREIGN PATENT DOCUMENTS

| | | | |
|---|---|---|---|
| CN | 1934776 A | 3/2007 | ............. H02N 11/00 |
| DE | 199 12 606 | 12/2000 | ............. F04B 43/04 |
| EP | 0 723 982 | 7/1996 | ............. C08G 59/56 |
| EP | 0 736 556 | 10/1996 | ............. C08G 59/00 |
| EP | 0882890 | 12/1998 | ............. F04B 45/053 |
| EP | 1 454 935 | 9/2004 | ............. C08G 59/00 |
| JP | 58-25326 | 2/1983 | |
| JP | 60-235847 | 11/1985 | |
| JP | 02-004826 | 1/1990 | |
| JP | 02 137 930 | 5/1990 | ............. B41J 2/05 |
| JP | 08-283540 | 10/1996 | |
| JP | 09 287 571 | 11/1997 | ............. F04B 43/04 |
| JP | 2004-514770 | 5/2004 | |
| JP | 2004-261045 | 9/2004 | |
| JP | 2004-269882 | 9/2004 | |
| JP | 2005269773 | 9/2005 | ............. F03G 7/00 |
| JP | 2006353034 | 12/2006 | ............. H02N 2/00 |
| JP | 2008211915 | 9/2008 | ............. F03G 7/00 |
| JP | 2009046649 | 3/2009 | ............. C08F 12/34 |
| WO | WO 96/17170 | 6/1996 | ............. F04B 35/00 |
| WO | WO 96/20971 | 7/1996 | ............. C08G 63/00 |
| WO | WO 97/42412 | 11/1997 | ............. F04B 43/12 |
| WO | WO 00/28215 | 5/2000 | ............. F04B 45/047 |
| WO | WO 02/44240 | 6/2002 | ............. C08G 59/40 |
| WO | WO 2004/031581 | 4/2004 | |
| WO | WO 2004/076859 | 9/2004 | ............. F04B 43/04 |
| WO | WO 2005/061014 | 7/2005 | |
| WO | WO 2005/118008 | 12/2005 | |
| WO | WO 2006/065884 | 6/2006 | |
| WO | WO2006/065884 | 6/2006 | |
| WO | WO 2006065884 A2 * | 6/2006 | |
| WO | WO 2008/079440 | 7/2008 | ............. C08L 63/10 |
| WO | WO2008129549 | 10/2008 | ............. A61M 5/148 |
| WO | WO 2009/069086 | 6/2009 | |
| WO | WO2011032011 | 3/2011 | ............. A61M 5/142 |

OTHER PUBLICATIONS

Yoshioka, Yuka and Calbert, Paul, "Epoxy-Based Electroactive Polymer Gels", Experimental Mechanics, Dec. 2002, vol. 45, No. 5.
PCT International Search Report and International Preliminary Report on Patentability, dated Oct. 25, 2006, PCT/US05/45210.
PCT International Search Report and International Preliminary Report on Patentability, dated Jul. 7, 2008, PCT/US07/73188.
PCT International Search Report and International Preliminary Report on Patentability, dated Feb. 19, 2009, PCT/US08/85421.
Indian Examination Report; Indian Patent Application Serial No. 2371/CHENP/2005, dated Sep. 7, 2006.
Official Action, U.S. Appl. No. 11/721,800, dated Aug. 27, 2010.
Unsolicited letter from Dr. Elson Silva, dated Oct. 21, 2010 (5 pages).
"An Electrochemical Microactuator: Principle and First Results", Neagu et al. Journal of Microelectromechanical Systems, vol. 5, No. 1, Mar. 1996 (7 pgs).
"ElectroActive Polymers—EAPs," downloaded from http://www.azom.com on Dec. 16, 2013 (5 pgs).
"Epoxy-Based Electroactive Polymer Gels", Yoshioka Y and Calvert P, Experimental Mechanics, vol. 42, No. 4, Dec. 2002, pp. 404-408 (5 pgs).
"Magnetic Driven Compression Cascade and Packaging", IBM Technical Disclosure Bulletin, IBM Corp., col. 38, co. 1, Jan. 1995 (3 pgs).
"Micro-Dispensing Positive Displacement Pump", Anonymous, Research Disclosure, Mason Publications, Hampshire GB, vol. 374, No. 4, Jun. 1995 (9 pgs).
"Structure and Mechanism of Two Types of Micro-Pump Using Polymer Gel", Hattori et al., Micro Electro Mechanical Systems, 1992, MEMS 92, Proceedings. An Investigation of Micro Structures, Sensors, Actuators, Machines and Robot, IEEE Travemunde, Germany, Feb. 1992 (6 pgs).
Bar-Cohen, Y., "Electroactive polymers (EAP) actuators as artificial muscles: reality, potential and challenges," SPIE Press, 2001, 671 pgs, (book description only, 4 pgs).
Canadian Official Action issued in Appln. No. 2,557,325, dated Feb. 8, 2011 (5 pgs).
Chinese Notification of ReExamination and English translation, Appln. or Pat. No. 200580048306.3; dated Aug. 22, 2014 (11 pgs).
Chinese Office Action (w/English translation) issued in corresponding application No. 200780032137.3, dated Mar. 12, 2013 (14 pgs).
Chinese Office Action and Translation dated Jul. 6, 2011 issued in Chinese Patent Appln. No. 200780032137.3 (7 pgs).
Chinese Office Action issued Jul. 1, 2014 with English translation, Appln. No. or Patent No. 201180007957.3 (17 pgs).
Chinese Office Action, Application/Patent No. 200780032137.3, dated Dec. 23, 2011 (6 pgs).
Chinese Official Action + translation dated Feb. 1, 2011 issued in Appln. No. 200780032137.3, (8 pgs).
Chinese Official Action dated Mar. 17, 2011, Appln. No. 200580048306.3 (5 pgs).
Chinese Official Action issued in corresponding Chinese Patent Appln. Serial No. 200580048306.3 dated Nov. 4, 2011 (5 pgs).
European Office Action dated Sep. 14, 2010, Appln. No. 07 872 242.8 -2102, (6 pgs).
European Official Action issued in Appln. No. 04714231.0, dated May 11, 2011 (2 pgs).
European Official Action issued in Appln. No. 04714231.0-2315/1611353, dated Oct. 4, 2010 (4 pgs).
European Official Action, Apr. 6, 2011 issued in Appln. No. 07 872 242.8-2102 (4 pages).
European Official Action, Aug. 29, 2011 issued in Appln. No. 07 872 242.8-2102 (6 pages).
European Search Report dated Feb. 18, 2011 issued in corresponding Appln. No. 10014840.2-2315 (7 pgs).
European Search Report dated Jun. 8, 2009, Serial No. 07872242.8-2102 (7 pgs).
First Examination Report dated Dec. 31, 2013, Indian Patent a plication No. 3011/CHENP/2007 (2 pgs).
Indian Examination Report; Indian Patent Application Serial No. 2371/CHENP/2005, dated Sep. 7, 2006 (2 pgs).
International Preliminary Report on Patentability issued in PCT/US10/48489 dated Mar. 13, 2012 (12 pgs).
International Search Report and Written Opinion issued in corresponding PCT Patent Appln. Serial No. PCT/US2012/057129 dated Apr. 1, 2014 ( 7 pgs).
International Search Report and Written Opinion of the International Search Authority issued in PCT/US09/34557, dated Apr. 13, 2009 (6 pgs).
Japanese Office Action with translation, Patent Appln. 2009-519642, dated Jul. 9, 2012 (9 pgs).
Office Action issued in related U.S. Appl. No. 10/786,718, dated Mar. 5, 2008 (41 pgs).

(56) References Cited

OTHER PUBLICATIONS

Office Action issued in related U.S. Appl. No. 10/786,718, dated Sep. 16, 2008 (8 pgs).
Office Action issued in related U.S. Appl. No. 10/786,718, dated Jan. 2, 2009 (9 pgs).
Office Action issued in related U.S. Appl. No. 10/786,718, dated Jul. 1, 2009 (7 pgs).
Office Action issued in related U.S. Appl. No. 10/786,718, dated Dec. 28, 2009 (6 pgs).
Office Action issued in related U.S. Appl. No. 10/786,718, dated May 5, 2010 (7 pgs).
Office Action issued in related U.S. Appl. No. 10/786,718, dated Sep. 15, 2010 (8 pgs).
Office Action issued in related U.S. Appl. No. 10/786,718, dated Nov. 23, 2010 (10 pgs).
Office Action issued in related U.S. Appl. No. 11/254,537, dated Sep. 17, 2007 (8 pgs).
Office Action issued in related U.S. Appl. No. 11/254,537, dated Mar. 4, 2008 (8 pgs).
Office Action issued in related U.S. Appl. No. 11/254,537, dated Jul. 21, 2008 (10 pgs).
Office Action issued in related U.S. Appl. No. 11/254,537, dated Dec. 15, 2008 (8 pgs).
Office Action issued in related U.S. Appl. No. 12/373,245, dated Feb. 2, 2011 (13 pgs).
Office Action issued in related U.S. Appl. No. 12/373,245, dated Jul. 22, 2011 (11 pgs).
Office Action issued in related U.S. Appl. No. 12/373,245, dated Jun. 30, 2014 (18 pgs).
Office Action issued in related U.S. Appl. No. 12/414,536, dated Nov. 29, 2010 (8 pgs).
Office Action issued in related U.S. Appl. No. 12/978,152, dated May 23, 2011 (9 pgs).
Office Action issued in related U.S. Appl. No. 13/018,024, dated Aug. 7, 2014 (17 pgs).
Office Action issued in related U.S. Appl. No. 13/093,648, dated Aug. 29, 2013 (5 pgs).
Office Action issued in related U.S. Appl. No. 13/395,627, dated Sep. 10, 2014 (9 pgs).
Office Action issued in related U.S. Appl. No. 13/424,172, dated Jun. 27, 2012 (14 pgs).
Office Action issued in related U.S. Appl. No. 13/424,172, dated Nov. 9, 2012 (6 pgs).
Office Action issued in related U.S. Appl. No. 14/071,371, dated Aug. 21, 2014 (16 pgs).
Office Action issued in related U.S. Appl. No. 12/745,880, dated Jun. 3, 2013 (8 pgs).
Office Action issued Nov. 23, 2012 in U.S. Appl. No. 12/745,880 (26 pgs.).
Official Action received in corresponding Chinese Application No. 200480010203.3, Sep. 14, 2007 (19 pgs).
Official Action received in corresponding Chinese Application No. 200480010203.3, Nov. 14, 2008 (5 pgs).
Official Action recieved in corresponding EPO Application. No. 04 714 231.0-2315, Nov. 13, 2008 (5 pgs).
Official Action, U.S. Appl. No. 11/721,800, dated Aug. 27, 2010 (13 pgs).
PCT International Preliminary Report on Patentability, dated Aug. 26, 2005, PCT/US04/005922 (11 pgs).
PCT International Search Report and Written Opinion, dated Oct. 22, 2004, PCT/US04/005922 (17 pgs).
PCT International Search Report and International Preliminary Report on Patentability, dated Oct. 25, 2006, PCT/US05/45210 (10 pgs).
PCT International Search Report and International Preliminary Report on Patentability, dated Jul. 7, 2008, PCT/US07/73188 (8 pgs).
PCT International Search Report and International Preliminary Report on Patentability, dated Feb. 19, 2009, PCT/US08/85421 (7 pgs).
PCT International Search Report and Written Opinion dated Mar. 28, 2011 PCT/US11/23375 (10 pgs).
PCT International Preliminary Report on Patentability issued in PCT/US2013/031062, dated Sep. 16, 2014 (9 pgs).
Search Report and Written Opinion received in Applicant's corresponding European Patent Application Serial No. 05854009.7, Nov. 11, 2009 (8 pgs).
Supplemental European Search Report issued in EP04714231, dated Jan. 25, 2007 (2 pgs).
Yoshioka et al., "Electrically Driven Miniature Hydrogels as Muscle-Like Acuators", 2001; Proceedings of SPIE vol. 4329, pp. 216-222 (7 pgs).
Office Action issued in related U.S. Appl. No. 14/071,371, dated Dec. 18, 2014 (11 pgs).
Japanese Office Action (with translation) issued in related application No. 2012-551386, dated Jan. 28, 2015 (9 pgs).
Office Action issued in related U.S. Appl. No. 13/395,627, dated Feb. 5, 2015 (7 pgs).
Chinese Board Decision, Appln. No. 200580048306.3, dated Dec. 26, 2014 (14 pgs).
Office Action issued in related U.S. Appl. No. 12/373,245, dated Feb. 9, 2015 (11 pgs).
Office Action issued in related U.S. Appl. No. 12/918,466, dated Jul. 11, 2013 (36 pgs).
India Hearing Notice in Reference of Application No. 3011/CHENP/2007, dated Feb. 5, 2015 (1 pg).
Office Action issued in U.S. Appl. No. 13/018,024, dated Feb. 24, 2015 (31 pgs).
Office Action issued in U.S. Appl. No. 13/424,172, dated Jun. 10, 2015 (25 pgs).
Office Action issued in U.S. Appl. No. 14/347,597, dated Jun. 3, 2015 (33 pgs).
Indian Office Action issued in application No. 137/CHENP/2009, dated. Mar. 17, 2015 (2 pgs).
Office Action issued in U.S. Appl. No. 12/918,466, dated Nov. 19, 2015 (25 pgs).
Extended European Search Report issued in application No. 12836396.7, dated Nov. 10, 2015 (12 pgs).
Chinese Office Action (w/translation) issued in application No. 201380022758.9, dated Dec. 14, 2015 (12 pgs).
Banister et al., "Molecular Engineering of Polymer Actuators for Biomedical and Industrial Use," Electroactive Polymer Actuators and Devices (EAPAD) 2012, vol. 8340 (20 pgs).
Notice of Allowance issued in U.S. Appl. No. 13/395,627, dated Sep. 16, 2015 (22 pgs).
Office Action issued in U.S. Appl. No. 12/373,245, dated Sep. 9, 2015 (20 pgs).
Chinese Office Action issued in application No. 201280057499.9, dated Aug. 28, 2015 (13 pgs).
Indian Office Action issued in application No. 137/CHENP/2009, dated Oct. 29, 2015 (2 pgs).
Office Action issued in U.S. Appl. No. 12/745,880, dated Jul. 22, 2015 (23 pgs).
Chinese Office Action issued in application No. 201180007957.3, dated May 22, 2015 (11 pgs).
Office Action issued in U.S. Appl. No. 13/018,024, dated Aug. 4, 2015 (10 pgs).
Chinese Office Action issued in application No. 201180007957.3, dated Feb. 15, 2016 (12 pgs).
Chinese Office Action issued in application No. 201280057499.9, dated Jun. 28, 2016 (13 pgs).
European Office Action issued in application No. 13 760 829.5, dated Jan. 26, 2016 (4 pgs).
Notice of Allowance issued in U.S. Appl. No. 13/018,024, dated Mar. 2, 2016 (24 pgs).
Office Action issued in U.S. Appl. No. 12/373,245, dated Jun. 1, 2016 (17 pgs).
Office Action issued in U.S. Appl. No. 13/424,172, dated Feb. 24, 2016 (22 pgs).
Office Action issued in U.S. Appl. No. 14/347,597, dated Feb. 25, 2016 (32 pgs).

(56) References Cited

OTHER PUBLICATIONS

Office Action issued in U.S. Appl. No. 14/385,403, dated. Mar. 30, 2016 (32 pgs).

* cited by examiner

FLUID METERING DEVICE

CROSS REFERENCE TO RELATED APPLICATIONS

This application claims priority from PCT Patent Application Serial No. PCT/US08/85421 filed Dec. 3, 2008, which claims priority from U.S. Provisional Application Ser. No. 60/992,003, filed Dec. 3, 2007, the contents of which are incorporated herein by reference.

The invention is a fluid metering device or pump that can deliver a pre-determined volume of fluid at a pre-determined pressure at a pre-determined rate of delivery. The device can be pre filled with the fluid during the manufacturing process or the device can be manufactured empty to be filled at a later time. The device can also meter multiple fluids in separate reservoirs at the same time and mix the fluids, if needed. The invention has particular utility as a device for metering drugs and will be described in connection with such utility, although other utilities are contemplated.

This invention also includes further modifications and improvements of US pending application 20040234401, now abandoned, PCT application US2004/005922, PCT application US05/045210 and PCT application US07/73188 which are herein included in this application in their entirety.

Controlled delivery of fluids, such as drugs, in the medical and veterinary fields is accomplished by a variety of methods. One method of controlled prolonged delivery of beneficial agents involves the use of osmotic delivery systems. These devices can be external devices or implanted to release beneficial agents in a controlled manner over a pre-selected time or administration period. In general, osmotic delivery systems operate by absorbing fluid from the outside environment and releasing corresponding amounts of the beneficial agent. These devices are somewhat limited in use and practicality due to inaccuracies or delays in the time it takes for the device to absorb a fluid and start expelling fluid flow out of the device. This delay is caused by air pockets or voids that remain and get compressed during the start of the pump process Delayed start-up of beneficial fluids delivery is a significant problem in osmotic delivery systems.

This problem is solved by using a flexible actuator material that can be compressed when pump is assembled, creating a preloaded pressure condition that negates any dead airspace compression issues, that can delay the time it takes to start expelling the beneficial fluids. Because the actuator is already under pressure it starts delivering fluids as soon as the fluids are released from any restrictions on the fluid tubing, as the material relaxes outwardly when released. This allows time for the actuator material to start absorbing the hydrating fluids.

Another problem with osmotic pumps is that osmotic pressure often is too low to deliver many of the new more viscous pharmaceutical agents and materials. Methods and materials are described that overcome the osmotic pressure issues with the introduction of protonated molecular repulsive forces, that occur upon hydration of the flexible actuator material and can produce pressures in excess 50 psi. easily delivering most fluids.

Another problem that is solved by a flexible actuator material is that the device can now be made itself of flexible materials as long as these materials are, less flexible, or stiffer than the actuator material, the more flexible a device is the more desirable it is for comfort of the patient, animal or package configuration.

The invention in broad aspect provides a device for metering fluids comprising a fluid chamber with one inlet or outlet port, at last one sidewall and a movable separator that is in contact with and separates the fluid in the chamber from the other components of the device. The device includes a porous actuator housing and wicking material, a flexible polymer actuator material in contact with the porous actuator housing and the moveable separator, an actuator hydrating solution reservoir with at least one sidewall, an inlet port, and in fluid contact with porous actuator housing, and a fluid gate located at some point between actuator hydrating solution reservoir and the polymer actuator, effectively keeping the polymer actuator dry. An external shell holds all components on that the polymer actuator can only move in a direction and apply pressure to the separator in contact with the fluid in the fluid chamber, thereby dispensing fluid from fluid chamber.

In one aspect of the invention the fluid chamber is removable.

In another aspect of the invention the fluid chamber is made of a plastic, metal, glass, ceramic carbon or combination of these materials.

In another aspect of the invention the fluid chamber inlet/outlet port is capped or sealed by a pierce able septum.

In another aspect of the invention the movable separator is a rubber plunger.

In another aspect of the invention the movable separator is an elastomeric membrane and also a part of or attached to the fluid chamber.

In another aspect of the invention the porous actuator housing is made from plastic, metal, glass, ceramic, carbon or combination of these materials.

In another aspect of the invention the polymer actuator material is removable.

In another aspect of the invention the polymer actuator material is hydrophilic, or is a combination of hydrophilic and hydrophobic materials.

In another aspect of the invention the polymer actuator material, fluid gate, porous actuator housing, actuator hydrating solution reservoir are enclosed together as a sealed unit with an elastic membrane in contact with actuator material, with a port covered by a pierce able septum that allows filling and venting of the actuator hydrating solution reservoir with actuator hydrating solution.

In another aspect of the invention the fluid gate stopping actuator hydrating solution from contacting actuator is removable by the following methods of piercing, dissolving, tearing, pushing or by pulling gate out of hydrating solution path to allow hydration of the polymer actuator.

In another aspect of the invention the fluid gate is a membrane that can be torn, pierced or dissolved.

In another aspect of the invention the fluid gate can be opened and closed like a valve.

In another aspect of the invention the fluid in the fluid chamber is a medicine or has therapeutic value.

In another aspect of the invention the fluid camber can be filled in the device.

In another aspect of the invention the fluid chamber septum is pierced and the fluid is released into tubing that is in contact with a person or patient via a needle or other method that allows metering of released fluid to desired contact point.

In another aspect of the invention the fluid chamber septum is pierced and the fluid is released into tubing that is in contact with an animal via a needle or other method that allows metering of released fluid to desired contact point.

In another aspect of the invention the actuator material has varying layers of density and porosity.

In another aspect of the invention the actuator material has reacted and unreacted molecular sites.

In another aspect of the invention the actuator material has varying degrees of reacted and unreacted molecular sites.

In another aspect of the invention the actuator materials ratio of reacted to unreacted molecular sites determines the speed and pressure generation of the actuator material.

In another aspect of the invention protonation of reactive molecular sites within the actuator material, by interaction with the actuator hydrating solution or chemical byproduct of that interaction, determines the speed and pressure generation of the actuator material.

In another aspect of the invention the actuator materials density or porosity determines the speed and pressure generation of the actuator material.

In another aspect of the invention the amount of surface area of the actuator surface in fluid contact with the actuator hydrating solution via the porous actuator housing wicking material determines the speed and pressure generation of the actuator material.

In another aspect of the invention the actuator hydrating solution pH or chemical makeup determines the speed and pressure generation of the actuator material.

In another aspect of the invention, the device is implantable into a person, patient or animal.

In another aspect of the invention, the device utilizes body fluids as the actuator hydrating solution and has an opening in the exterior shell that allows the uptake of fluids by the actuator material.

The invention also provides in an alternative a device for metering fluids comprising two or more separate fluid chambers with one inlet or outlet port, at least one sidewall and a movable separator that is in contact with and separates the fluid in the fluid chambers from the other components of the device. The device includes a porous actuator housing and wicking material, a flexible polymer actuator material in contact with the porous actuator housing and the moveable separators, an actuator hydrating solution reservoir with at least one sidewall, an inlet port, and in fluid contact with porous actuator housing, a fluid gate located between each actuator hydrating solution reservoir and the polymer actuator. An external shell holds all components so that the polymer actuator can only move in a direction and apply pressure to the separator in contact with the fluid in the fluid chamber, thereby dispensing fluid from fluid chambers.

In one aspect of the alternative device one or more of the fluid chambers are removable.

In another aspect of the alternative device one or more of the fluid chambers are made of a plastic, metal, glass, ceramic carbon or combination of these materials.

In another aspect of the alternative device one or more of the fluid chambers inlet/outlet ports are capped or sealed by a pierce able septum.

In another aspect of the alternative device the movable separator is a rubber plunger.

In another aspect of the alternative device the movable separator is an elastomeric membrane and also a part of the fluid chamber.

In another aspect of the alternative device the porous actuator housing is made from plastic, metal, glass, ceramic, carbon or combination of these materials.

In another aspect of the alternative device the polymer actuator material is removable In another aspect of the alternative device the polymer actuator material is hydrophilic, or is a combination of hydrophilic and hydrophobic materials.

In another aspect of the alternative device the polymer actuator material, fluid gate, porous actuator housing, actuator hydrating solution reservoir are enclosed together as a sealed unit with an elastic membrane in contact with actuator material, with a port covered by a pierce able septum that allows filling and venting of the actuator hydrating solution reservoir with actuator hydrating solution.

In another aspect of the alternative device the fluid gate stopping actuator hydrating solution from contacting actuator is removable or broken by the following methods piercing, dissolving, tearing, pushing or by pulling gate out of hydrating solution path to allow hydration of the polymer actuator.

In another aspect of the alternative device the fluid gate is a membrane that can be torn, pierced or dissolved.

In another aspect of the alternative device the fluid gate can be opened and closed like a valve.

In another aspect of the alternative device the fluids in the fluid chambers are a medicine or have therapeutic value.

In another aspect of the alternative device the fluid chambers can be filled in the device.

In another aspect of the alternative device the fluid chamber septums are pierced and the fluid is released into tubing that is in contact with a person or patient via a needle or other method that allows metering of released fluid to desired contact point.

In another aspect of the alternative device the fluid chamber septum is pierced and the fluid is released into tubing that is in contact with an animal via a needle or other method that allows metering of released fluid to desired contact point.

In another aspect of the alternative device the actuator material is an epoxy.

In another aspect of the alternative device the actuator material has varying layers of density and porosity.

In another aspect of the alternative device the actuator material has reacted and unreacted molecular sites.

In another aspect of the alternative device the actuator material has varying degrees of reacted and unreacted molecular sites.

In another aspect of the alternative device the actuator materials ratio of reacted to unreacted molecular sites determines the speed and pressure generation of the actuator material.

In another aspect of the alternative device the actuator materials density or porosity determines the speed and pressure generation of the actuator material.

In another aspect of the alternative device the amount of surface area of the actuator surface in fluid contact with the actuator hydrating solution via the porous actuator housing wicking material determines the speed and pressure generation of the actuator material In another aspect of the alternative device the actuator hydrating solutions pH or chemical makeup determines the speed and pressure generation of the actuator material.

In another aspect of the alternative device there are one or more different actuator materials providing different speeds and pressures for one or more fluid chambers.

In yet another aspect of the alternative embodiment, the device is implantable into a person, patient or animal.

In the latter embodiment, the device utilizes body fluids as the actuator hydrating solution and has an opening in the exterior shell that allows the uptake of body fluids by the actuator material.

In still yet another embodiment of the invention there is provided a device for metering fluids comprising two or more separate fluid chambers with one or more inlet or outlet ports that are in fluid connection with a mixing chamber, and have at least one sidewall and a movable separator that is in contact with and separates the fluid in the fluid chambers from the other components of the device. The device includes a mixing chamber with one or more inlet port openings that are in fluid contact with the fluid chambers, and an exit port opening, that is in fluid contact with tubing or fluid channel or method to transport mixed fluids to desired delivery site. A porous actuator housing and wicking material, a flexible polymer actuator material in contact with the porous actuator housing and the moveable separators, an actuator hydrating solution reservoir with at least one sidewall, an inlet port, and in fluid contact with porous actuator housing, a fluid gate located between each actuator hydrating solution reservoir and the polymer actuator. An external shell holds all components so that the polymer actuator can only move in a direction and apply pressure to the separator in contact with the fluid in the fluid chamber, thereby dispensing fluid from fluid chambers.

In the still yet another embodiment one or more of the fluid chambers are made of a plastic, metal, glass, ceramic carbon or combination of these materials.

In the still yet another embodiment one or more of the fluid chambers inlet/outlet ports are capped or sealed by a pierce able septum.

In the still yet another embodiment the movable separator is a rubber plunger.

In the still yet another embodiment the movable separator is an elastomeric membrane and also a part of the fluid chamber.

In the still yet another embodiment the porous actuator housing is made from plastic, metal, glass, ceramic, carbon or combination of these materials.

In the still yet another embodiment the polymer actuator material is removable

In the still yet another embodiment the polymer actuator material is hydrophilic or is a combination of hydrophilic and hydrophobic materials.

In the still yet another embodiment the polymer actuator material, fluid gate, porous actuator housing, actuator hydrating solution reservoir are enclosed together as a sealed unit with an elastic membrane in contact with actuator material, with a port covered by a pierce able septum that allows filling and venting of the actuator hydrating solution reservoir with actuator hydrating solution.

In the still yet another embodiment the fluid gate stopping actuator hydrating solution from contacting actuator is removable or broken by the following methods piercing, dissolving, tearing, pushing or by pulling gate out of hydrating solution path to allow hydration of the polymer actuator.

In the still yet another embodiment the fluid gate is a membrane that can be torn, pierced or dissolved.

In the still yet another embodiment the fluid gate can be opened and closed like a valve.

In the still yet another embodiment the fluids in the fluid chambers are a medicine or have therapeutic value.

In the still yet another embodiment the fluid cambers can be filled in the device.

In the still yet another embodiment the mixing chamber exit port is capped or sealed by a septum, septum is pierced and the fluid is released into tubing that is in contact with a person or patient via a needle or other method that allows metering of released fluid to desired contact point.

In the still yet another embodiment the mixing chamber exit port is capped or sealed by a septum, septum is pierced and the fluid is released into tubing that is in contact with an animal via a needle or other method that allows metering of released fluid to desired contact point.

In the still yet another embodiment the actuator material is an epoxy.

In the still yet another embodiment the actuator material has varying layers of density and porosity.

In the still yet another embodiment the actuator material has reacted and un-reacted molecular sites.

In the still yet another embodiment the actuator material has varying degrees of reacted and un-reacted molecular sites.

In the still yet another embodiment the actuator materials ratio of reacted to un-reacted molecular sites determines the speed and pressure generation of the actuator material.

In the still yet another embodiment the actuator materials density or porosity determines the speed and pressure generation of the actuator material.

In the still yet another embodiment the amount of surface area of the actuator surface in fluid contact with the actuator hydrating solution via the porous actuator housing wicking material determines the speed and pressure generation of the actuator material In the still yet another embodiment the actuator hydrating solutions pH or chemical makeup determines the speed and pressure generation of the actuator material.

In the still yet another embodiment there are one or more different actuator materials providing different speeds and pressures for one or more fluid chambers.

In yet another embodiment, the device is implantable into a person, patient or animal.

In the latter embodiment, the device utilizes body fluids as the actuator hydrating solution and has an opening in the exterior shell that allows the uptake of body fluids by the actuator material.

In yet another embodiment of the invention a two part insulin is mixed together at the prescribed ratio and metered after mixing to a patient via subcutaneous delivery.

In still yet another embodiment of the invention multiple types of medication, gene therapies, proteins etc. are metered to a patient via the best route to deliver the particular medications at the desired site on or in the patient.

Further features and advantages of the present invention will be seen from the following detailed description, taken in conjunction with the accompanying drawings, wherein FIG. 1 schematically illustrates a representative embodiment of the invention.

Figure 1:
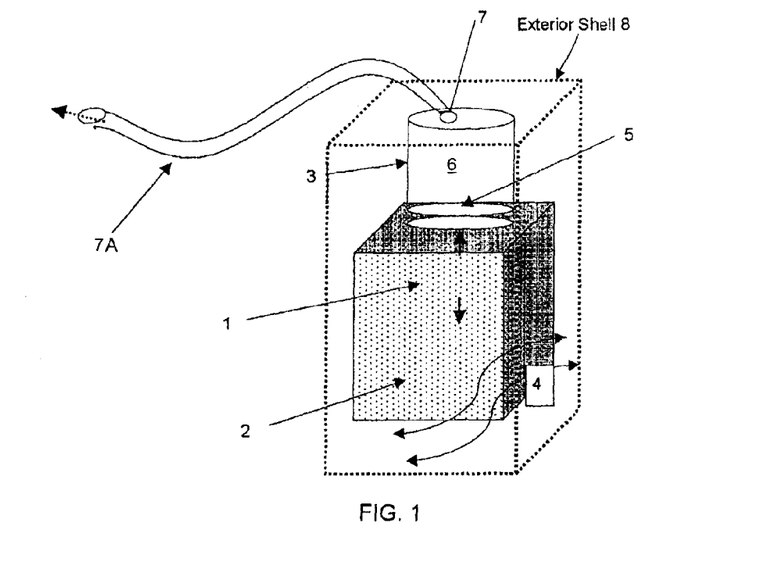
Figure 2:
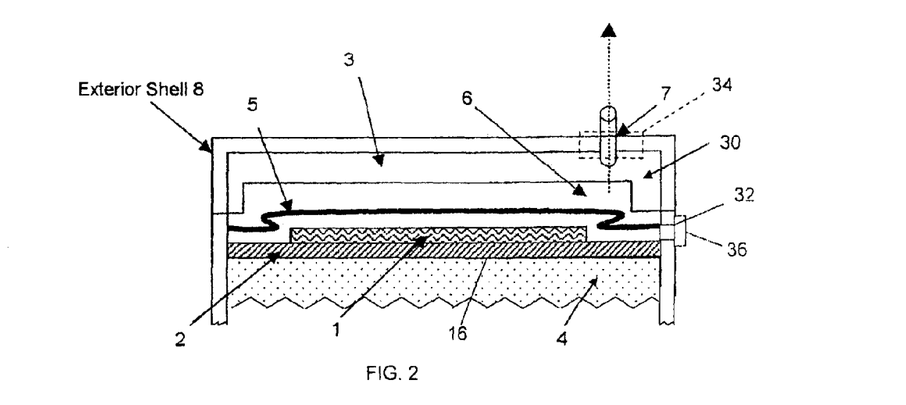
FIG. 2 is a side cross-sectional view of an embodiment of the invention.
Figure 2A:
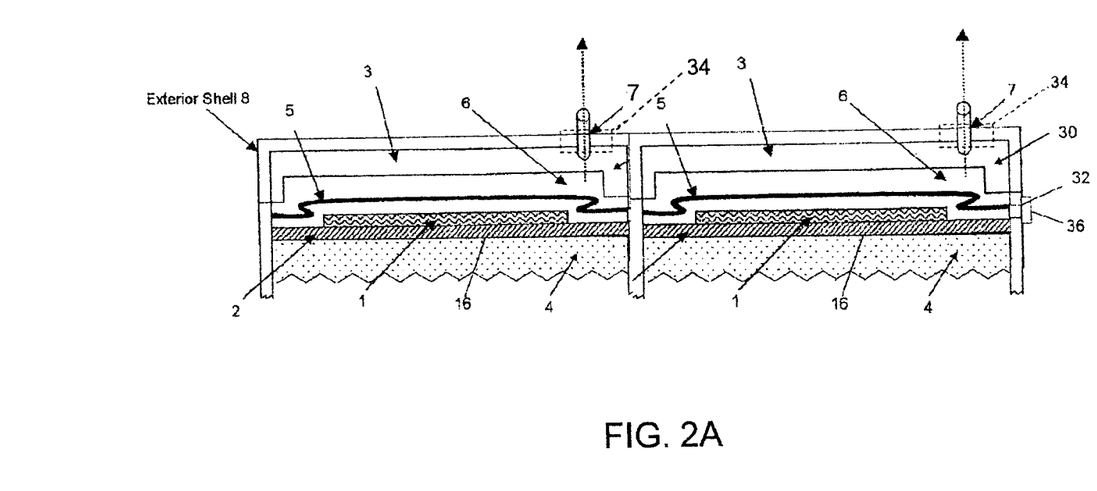
FIG. 2A is a view similar to FIG. 2 of a second embodiment of the invention.

Referring to the drawings, the present invention in one aspect comprises a chamber made in two parts that are assembled together with one or more inlet or outlet ports or openings (7) having tubing (7A) extended therethrough that are in fluid or gaseous connection with a mixing chamber 30. The displacement of the volume in the chamber is accomplished by using one or more but not limited to, polymers, co polymers, block polymers, hydro gels or epoxy materials that are hydrophilic and used as actuator material (1). For ease of illustration, FIG. 1 and FIG. 2 are not drawn to scale. Also, the exterior shell wall is illustrated in phantom in one dimension. The actuator material reacts by degrees of swelling to the chemical composition of the solution (4) hydrating the actuator material. The actuator hydrating fluid can range in pH from 0-14, depending on the actuator material, degree of swelling, pressure and displacement time required for the desired performance of the invention. The actuator material hydrating solution is kept separate from the fluid or gas being pumped or displaced by a flexible or moveable membrane, elastomeric or plunger material (5) that can stretch, move or slide as the fluid or gas volume (6) in the chamber is displaced by the actuator expansion or contraction and continue to keep a fluid or gas seal between the actuator hydrating fluid and the fluid or gas being pumped. The fluid chamber inlet and/or outlet may be capped or sealed by a piercable septum as shown in phantom at 34 in FIG. 2. FIG. 2A is similar to FIG. 2, but comprises two separate walled chambers with one or more fluid inlet or fluid outlet ports that are in fluid connection with a mixing chamber, etc., as described for FIG. 2.

One part of the ph responsive metering device or pump has one or more polymer actuator materials housed within or on a porous media substrate (2) that is less flexible than the actuator material. The second part of the chamber is a hollow shell, cavity or cylinder (3) made from material that is also less flexible than the actuator material. These fluid chamber materials can be made of but not limited to plastics, elastomeric material, glass, ceramics, metals and combinations of these. These are then housed in an external shell (8) for the form factor. All of the materials are standard in the relevant industry the device is used in and the performance requirements of the fluid or gaseous metering device or pump and are well known to experts in each field of use.

In one preferred embodiment, a flexible patch for liquid drug delivery, all of the parts are assembled by lamination techniques well know in the plastics industry, such as but not limited to glue, heat, pressure, UV irradiation, RF, or sonic welding. In the case of a cylinder or tube a. movable but fluid sealing plunger or piston (18) may be used. An example of this is a pre-filled medication vial or syringe such as but not limited to, the 3 ml glass vials or syringes used for insulin with an exit port covered by, capped or sealed by a septum shown at (20) at the chamber outlet end and rubber stopper that is pushed to dispense the fluid at the opposite end, which is open. The moveable rubber plunger or stopper keeps a sterile fluid seal but can be pushed to displace or dispense the medication once the septum is pierced and the medication is in fluid connection with a tube or needle that is able to inject medication into the patient. In both examples the fluid being metered or pumped is separate from the fluid used to hydrate the actuation material. The porous media is a ridged or semi ridged substrate or housing for the actuator material, it is also a fluid conduit to hydrate the actuator material. The porous material can be molded, extruded or stamped to allow geometric flexibility of the con figuration that makes up the complete device.

For example a medical device that uses industry standard medication vials such as but not limited to the 3 ml glass insulin vials or syringes, is typically referred to as an insulin syringe pump. These pumps are electronically controlled and driven by electric motors that turn very precise screw mechanisms in increments to push the syringe stopper and deliver small incremental doses of the insulin over a pre programmed time and rate.

The ph responsive pump uses the migration of the desired ph chemical solution through the polymer matrix and the resulting expansion or contraction as the mechanism to push the syringe stopper. As the polymer matrix expands or contracts it produces continuous pressure thereby offering continuous delivery rates. The speed of this reaction can be increased or decreased several ways.

By increasing the porosity of the polymer the speed increases or by decreasing the porosity of the polymer the actuation speed is decreased. The actuator material porosity can be adjusted by changing ratios of materials, adding catalysts or other materials that can be washed out with a solvent after the polymerization process, many methods are used dependent on the materials being used to make the actuator material and are well known within the polymer industry.

Figure 3:
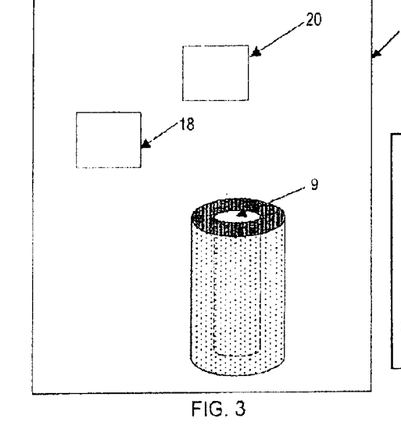
FIG. 3 shows a single actuator.
Figure 4:
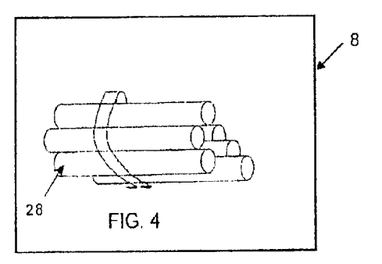
FIG. 4 shows a plurality of actuators.
Figure 5:
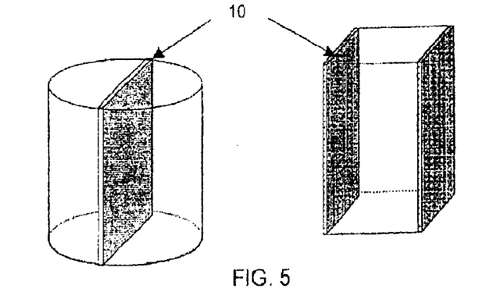
FIG. 5 illustrates another embodiment of the invention.

By increasing available external surface area of the actuator material the speed increases, the reverse is also true if you decrease available surface area, one way this is accomplished by stacking or assembling actuators together. For example a bundle of round strands (28) of actuator material provides a large amount of external surface area for rapid fluid migration, yet still provides good pushing force as it expands. Another actuator configuration to increase surface area is a hollow tube (9), as the actuator expands it is omni-directional and the center of a tube of the material allows a conduit for rapid uptake of fluid until it closes from the expansion.

In another preferred actuator or device configuration a fluid wicking material (10) that can be ridged, flexible or elastomeric is used. The wicking material adds a uniform fluid conduit or channel internally, through, along, in between or externally around the actuator material. The wicking material can be a hydrophobic or hydrophilic material that is compatible to the chemical fluid hydrating the actuator material. By inserting a wicking material either into or around the porous actuator material (not shown for the sake of simplifying the drawings) it provides a uniform hydration method that provides continuous pressure at the desired speed of expansion or contraction which results in a linear rate of fluid or gas displacement from the pump chamber. This solves the problem of increasing or decreasing pump or metering rate curves that develop as the actuator material expands or contracts and ratio of actuator surface area or exposed footprint to the actuator hydration fluid changes.

Yet another preferred actuation material configuration is a foamed actuator material this allows fast uptake of fluids, like a sponge, which results in faster actuation cycles or times. The increased surface area can also increases reaction surface area of the material, for example by incorporating primary, secondary or combinations of amines or other functional molecular groups in a polymer or actuator material, results in enhanced performance characteristics as the amines react to the ph of the hydrating solution in conjunction with the hydration effects of the actuator material.

The foaming can be accomplished by but not limited to the use of catalysts, emulsifiers, foaming agents, colloidal suspensions, heating, peroxides even whipping air into the liquid materials during polymerization can produce foamed actuation material. Oxidizing materials incorporated to add desired performance characteristics to the actuator materials can also result in foaming, these techniques are well known in the chemical and polymer industry.

Another preferred actuator material configuration is graduated porosity of the material. This actuator material can be made in one piece or by stacking layers of materials of different porosities and compositions together. One way of producing a one piece material is by adding layers of different porosity liquid actuator material into a mold, while still liquid each layer will mix slightly with the layer already in the mold and then the material can be polymerized or cured to produce the actuator material. Another way to produce the graduated porosity material is to pour each layer one at a time in the same mold, polymerize or cure it, then add the next liquid material layer and polymerize or cure it and continue adding layers until finished.

In another preferred embodiment the actuator material is kept dry and attached to the porous material or housed in it. The actuator hydrating solution is stored or kept separate from the actuator material by a thin film that is burst, pierced or dissolved when the device is started. The fluid is absorbed by or flows through the porous material and starts hydrating the actuator material starting the pumping or dispensing action. The embodiment also envisions having dissolving or time release capsules that can change the ph of the solution over time as the dissolve in the actuator hydrating solution, for example polymer actuators that have amines incorporated turn the hydrating solution to a basic ph of 9 or 10 over time, a slowly dissolving acidic chemical would extend and get the maximum time and pressure needed by the device because the amines react to the degree of the acid in the solution, these are all ways to control or engineer the performance of the device for a specific application.

Multiple actuators are another embodiment of the devices. The actuators are positioned in line or sequence. Sealed sections hold the actuator material and keep the actuator hydrating solution from each of the next in line or sequenced actuators. The pressure generated over time by the actuator material is used to open the next seal via puncture, bursting or physically opening a valve to allow fluid into the next section and to the actuator material and a progression of the actuators and actuator fluid can be controlled this way to engineer the performance of the devices for applications.

Preferred embodiments of the complete devices include a disposable one time liquid drug delivery patch that can be flexible and use disease, industry or manufacturers specific delivery routes or skin barrier technology to delivery the liquid drug through the patients skin and into the patient, for example a subcutaneous injection or infusion via needle and tubing another method is micro needle array, yet another is ionophoresis.

Another device embodiment is a one use cartridge that dispenses an industry or manufacturer's specific pre loaded liquid drug container and uses disease, industry or manufacturer's specific delivery routes to the patient, for example Insulin for diabetes can be delivered via a subcutaneous injection or infusion via needle and tubing in fluid connection to the drug container. By using a preloaded 3 ml vial of insulin the device can deliver a continuous pre determined rate of insulin to the patient, this is accomplished by the expansion characteristics of the actuator material that is used in the device to displace the insulin in the preloaded insulin vial.

Other device embodiments can also deliver bolus doses to the patient by have a predetermined bolus dose volume chamber in fluid connection with the delivery route and incorporating one way valves. A flexible membrane or covering that will deflect back to original shape once pressed is attached to one side or part of the bolus dose chamber and is physically pressed by the patient to dispense the bolus volume when needed. The one way valves allow the fluid to only travel in only one direction, towards the patient, to empty the bolus chamber and then the negative pressure in the dispensed chamber draws more fluid in from the fluid container over a predetermined time to refill bolus chamber for next bolus dose. Patient administered bolus doses are needed in many therapeutic protocols, pain and diabetes are examples of this need.

Other devices are envisioned that can use multiple liquid drug containers at the same time and mix the liquids prior to delivery or deliver separate liquids at different rates and pressures to the patient either directly as described above, or indirectly such as dispensing into an IV line or bag that will be or is attached to the patient and is delivering larger volumes of liquid drugs, hydrating or nutritional fluids. Chemotherapy, 2 part insulin, and antibiotics are all therapies that need this ability.

There are also many non medical uses for these devices such as pumping, mixing or dispensing chemicals over an extended period of time at predetermined rates. Mixing and dispensing 2 and 3 part epoxies at predetermined rates etc. The use of metering of gasses and gaseous flows can also be accomplished and is envisioned by the described inventions. The ability to engineer a device that produces a predetermined pressure at a predetermined rate over a predetermined time is very advantageous as many chemicals, glues, epoxies etc. are different viscosities so require the ability to be pumped or delivered at different pressures and rates.

The described inventions and components allow fluids and gaseous materials to be metered, pumped or dispensed in a low cost yet very accurate manner over extended time frames and pressures if needed. Multiple forms of the invention are described and are not meant to limit the scope of the inventions in any manner, shape, form factor or use.

The specific embodiments disclosed and illustrated herein should not be considered as limiting the scope of the invention, as understood by a person having ordinary skill in the art. Numerous variations are possible without falling outside the scope of the appended claims. The subject matter of the invention includes all novel and nonobvious combinations and subcombinations of the various elements, features, functions, and/or properties disclosed herein.

We claim:

1. A device for metering a fluid comprising a walled fluid chamber with at least one fluid inlet or fluid outlet port, at least one chamber wall and a movable separator that is in contact with and retains the fluid in the chamber, a porous media substrate and a wicking material, an actuator formed of a flexible polymer material in contact with the porous media substrate and with the moveable separator, an actuator hydrating solution reservoir bounded by said at least one chamber wall and a hydrating solution inlet port, in fluid contact with the porous media substrate, a fluid gate located between the actuator hydrating solution reservoir and the polymer actuator, effectively keeping the actuator dry, contained in an external shell so that the actuator is adapted to move in a direction and apply pressure to the separator in contact with the fluid in the fluid chamber, thereby dispensing fluid from the fluid chamber, wherein the actuator is formed of a material having varying layers of density and porosity or varying degrees of reacted and unreacted molecular sites.

2. The device in claim 1 wherein the actuator hydrating solution has a pH or chemical makeup that effects a speed and pressure generation of the actuator material.

3. The device in claim 2, wherein the device is adapted to be implanted in a person or animal and utilizes body fluids as the actuator hydrating solution and the said hydrating inlet port in the exterior shell allows the uptake of fluids by the actuator material.

4. The device as claimed in claim 1, wherein the fluid chamber and/or the actuator is removable.

5. The device as claimed in claim 1, wherein the fluid chamber and/or the porous actuator housing is made of a material selected from the group consisting of a plastic, a metal, glass, a ceramic, a carbon or a combination thereof.

6. The device as claimed in claim 1, wherein the fluid chamber inlet and/or outlet port is capped or sealed by a pierceable septum.

7. The device as claimed in claim 1, wherein the movable separator is a rubber plunger.

8. The device as claimed in claim 1, wherein the movable separator is an elastomeric membrane and also a part of or attached to the fluid chamber.

9. The device as claimed in claim 1, wherein the actuator is formed of a hydrophilic polymer material or a combination of a hydrophilic material and an hydrophobic polymer material.

10. The device as claimed in claim 1, wherein the actuator, fluid gate, porous media substrate, and actuator hydrating solution reservoir are enclosed together as a sealed unit with an elastic membrane in contact with the actuator, and said hydrating solution inlet port is covered by a pierceable septum that allows filling and venting of the actuator hydrating solution reservoir with actuator hydrating solution.

11. The device as claimed in claim 1, wherein the fluid gate is compromisable by breaking, piercing, dissolving, tearing, pushing or pulling the gate out of the actuator hydrating solution to allow hydration of the actuator material.

12. The device as claimed in claim 1, wherein the fluid gate is a membrane.

13. The device as claimed in claim 1, wherein the fluid in the fluid chamber is a medicine or has therapeutic value.

14. The device as claimed in claim 1, wherein the fluid gate is adapted to be pierced and fluid released into tubing adapted for contact with a person or animal.

15. The device as claimed in claim 1, wherein the actuator hydrating solution has a ratio of reacted to unreacted molecular sites that effects a speed and pressure generation of the actuator.

16. The device as claimed in claim 1, wherein protonation of reactive molecular sites within the actuator material, by interaction with the actuator hydrating solution or chemical byproduct of that interaction, effects a speed and pressure generation of the actuator.

17. The device as claimed in claim 1, wherein a density or porosity of the actuator material effects a speed and pressure generation of the actuator.

18. The device as claimed in claim 1, wherein an amount of surface area of actuator surface in fluid contact with the actuator hydrating solution via the porous a wicking material effects a speed and pressure generation of the actuator.

19. The device as claimed in claim 1, wherein the device is adapted to be implanted into a person or animal.

20. A device for metering fluids comprising two or more separate fluid chambers with at least one fluid inlet or fluid outlet port, at least one chamber wall and a movable separator that is in contact with and retains the fluid in the fluid chambers, a porous media substrate and wicking material, an actuator formed of a flexible polymer material in contact with the porous media substrate and with the movable separators, an actuator hydrating solution reservoir bounded by said at least one chamber wall and a hydrating solution inlet port, in fluid contact with the porous media substrate, a fluid gate located between each actuator hydrating solution reservoir, and the actuator, contained in an external shell so that the actuator is adapted to move in a direction and apply pressure to the separator in contact with the fluid in the fluid chambers, thereby dispensing fluid from the fluid chambers, wherein the actuator is formed of a material having varying layers of density and porosity or varying degrees of reacted and unreacted molecular sites.

21. The device as claimed in claim 20, wherein the actuator hydrating solution pH or chemical makeup effects a speed and pressure generation of the actuator material.

22. The device as claimed in claim 21, wherein the device is adapted to be implanted into a person or animal, and utilizes body fluids as the actuator hydrating solution and the said hydrating inlet port in the exterior shell allows the uptake of body fluids by the actuator material.

23. The device as claimed in claim 20, wherein multiple types of medication, gene therapies or proteins are metered to a patient at a desired site on or in the patient.

24. The device as claimed in claim 20, wherein one or more of the fluid chambers and/or the porous actuator housing are made of a material selected from the group consisting of a plastic, a metal, glass, a ceramic, a carbon or a combination thereof.

25. The device as claimed in claim 20, wherein one or more of the fluid chambers inlet and/or outlet ports are capped or sealed by a pierceable septum.

26. The device as claimed in claim 20, wherein the movable separator is a rubber plunger.

27. The device as claimed in claim 20, wherein the movable separator is an elastomeric membrane and also a part of the fluid chamber.

28. The device as claimed in claim 20, wherein the actuator is formed of a hydrophilic polymer material or a combination of a hydrophilic and hydrophobic material.

29. The device as claimed in claim 20, wherein the actuator, fluid gate, the porous media substrate, and the actuator hydrating solution reservoir are enclosed together as a sealed unit with said movable separator in contact with the actuator with a port covered by a pierceable septum that allows filling and venting of the actuator hydrating solution reservoir with actuator hydrating solution.

30. The device as claimed in claim 20, wherein the fluid gate is compromisable by breaking, piercing, dissolving, tearing, pushing or pulling the gate out of way of the actuator hydrating solution to allow hydration of the actuator material.

31. The device as claimed in claim 20, wherein the fluid gate is a membrane.

32. The device as claimed in claim 20, wherein the fluids in the fluid chambers are a medicine or have a therapeutic value.

33. The device as claimed in claim 20, wherein the fluid gate is adapted to be pierced and fluid released into tubing that is in contact with a person or animal.

34. The device as claimed in claim 20, wherein the actuator is formed of an epoxy material.

35. The device as claimed in claim 20, wherein the actuator hydrating solution has a ratio of reacted to unreacted molecular sites that effects a speed and pressure generation of the actuator.

36. The device as claimed in claim 20, wherein a density or porosity of the actuator material effects a speed and pressure generation of the actuator.

37. The device as claimed in claim 20, wherein an amount of surface area of actuator surface in fluid contact with the actuator hydrating solution via the wicking material effects a speed and pressure generation of the actuator.

38. The device as claimed in claim 20, wherein the actuator comprises a bundle of two or more actuators formed of different materials providing different speeds and pressures for the fluid chambers.

39. The device as claimed in claim 20, wherein the device is adapted to be implanted into a person or animal.

40. A device for metering fluids comprising two or more separate fluid walled chambers with one or more fluid inlet or fluid outlet ports that are in fluid connection with a mixing chamber, and have at least one chamber wall and a movable separator that is in contact with and retains the fluid in the fluid chambers, said outlet port being in fluid contact with tubing or fluid channel to transport mixed fluids to a desired delivery site; a porous media substrate and wicking material, an actuator formed of a flexible polymer material in contact with a porous media substrate and with the moveable separators, an actuator hydrating solution reservoir bounded by said at least one chamber wall and a hydrating solution inlet port, in fluid contact with the porous media substrate, a fluid gate located between each actuator hydrating solution reservoir and the actuator, contained in an external shell so that the actuator is adapted to move in a direction and apply pressure to the separator in contact with the fluid in the fluid chamber, thereby dispensing fluid from the fluid chambers wherein the actuator is formed of a material having varying layers of density and porosity or varying degrees of reacted and unreacted molecular sites.

41. The device as claimed in claim 40, wherein the actuator hydrating solution pH or chemical makeup effects a speed and pressure generation of the actuator material.

42. The device as claimed in claim 41, wherein the device is adapted to be implanted in the body of a person or animal, and utilizes body fluids as the actuator hydrating solution and said hydrating inlet port in the exterior shell that allows an uptake of body fluids by the actuator material.

43. The device as claimed in claim 40, wherein multiple types of medication, gene therapies or proteins are metered to a patient at a desired site on or in the patient.

44. The device as claimed in claim 40, wherein one or more of the fluid chambers and/or the porous media substrate are made of a material selected from a plastic, a metal, glass, a ceramic, a carbon or a combination thereof.

45. The device as claimed in claim 40, wherein one or more of the fluid chambers inlet and/or outlet ports are capped or sealed by a pierceable septum.

46. The device as claimed in claim 40, wherein the movable separator is a rubber plunger.

47. The device as claimed in claim 40, wherein the movable separator is an elastomeric membrane and also a part of the fluid chamber.

48. The device as claimed in claim 40, wherein the polymer actuator is formed of an hydrophilic material or a combination of an hydrophilic and an hydrophobic material.

49. The device as claimed in claim 40, wherein the actuator, fluid gate, the porous media substrate, and the actuator hydrating solution reservoir are enclosed together as a sealed unit with the movable separator in contact the with actuator, with the hydration solution inlet port covered by a pierceable septum that allows filling and venting of the actuator hydrating solution reservoir with actuator hydrating solution.

50. The device as claimed in claim 40, wherein the fluid gate is compromisable by breaking, piercing, dissolving, tearing, pushing or pulling the fluid gate out of the actuator hydrating solution path to allow hydration of the actuator material.

51. The device as claimed in claim 40, wherein the fluid gate is a membrane.

52. The device as claimed in claim 40, wherein the fluids in the fluid chambers are a medicine or have therapeutic value.

53. The device as claimed in claim 40, wherein the fluid inlet or outlet port is capped or sealed by a septum adapted to be pierced and fluid released into tubing adapted for contact with a person or animal.

54. The device as claimed in claim 40, wherein the actuator is formed of an epoxy material.

55. The device as claimed in claim 40, wherein the actuator hydrating solution has a ratio of reacted to un-reacted molecular sites that effects a speed and pressure generation of the actuator material.

56. The device as claimed in claim 40, wherein a density or porosity of the actuator material effects a speed and pressure generation of the actuator material.

57. The device as claimed in claim 40, wherein an amount of surface area of actuator surface in fluid contact with the actuator hydrating solution via the porous actuator housing wicking material effects a speed and pressure generation of the actuator.

58. The device as claimed in claim 40, wherein there are two or more different actuator materials which effect speeds and pressures for the fluid chambers.

59. The device as claimed in claim 40, wherein the device is adapted to be implanted into a person or animal.

* * * * *